United States Patent [19]

Taguchi et al.

[11] Patent Number: 5,717,494
[45] Date of Patent: Feb. 10, 1998

[54] METHOD OF OPTICALLY MEASURING LIQUID IN POROUS MATERIAL

[75] Inventors: Takayuki Taguchi, Sanda; Shigeru Fujioka, Tokyo; Tadao Yamaguchi, Sanda; Hisashi Motokawa, Kyoto; Atsushi Hosotani, Kyoto; Makoto Morishita, Kyoto, all of Japan

[73] Assignees: Nihon Medi-Physics Co., Ltd., Hyogo-ken; Teramecs Co., Ltd., Osaka, both of Japan

[21] Appl. No.: 747,966

[22] Filed: Nov. 12, 1996

[30] Foreign Application Priority Data

Nov. 15, 1995 [JP] Japan ................... 7-321012

[51] Int. Cl.$^6$ ........................... G01N 21/00
[52] U.S. Cl. ............... 356/432; 356/73; 356/410; 356/417; 356/246
[58] Field of Search ............... 356/432, 73, 410, 356/417, 246

[56] References Cited

U.S. PATENT DOCUMENTS

| | | |
|---|---|---|
| 3,526,480 | 9/1970 | Findl et al. ................ 23/253 |
| 4,475,813 | 10/1984 | Munk ........................ 356/73 |
| 5,477,324 | 12/1995 | Bertholot et al. ........... 356/432 |
| 5,600,444 | 2/1997 | Tong ......................... 356/432 |

*Primary Examiner*—Frank G. Font
*Assistant Examiner*—Reginald A. Ratliff
*Attorney, Agent, or Firm*—Sughrue, Mion, Zinn, Macpeak & Seas, PLLC

[57] ABSTRACT

In a method of measuring optical characteristics of a component in a liquid impregnated in a porous material with no affection by the porous material, a light beam having an absorbable wavelength which is absorbed by the component in the liquid and a light beam having a wavelength which is longer than the absorbable wavelength are projected to the porous material, and a quantity of light having the wavelength which is absorbed by the component in the liquid is compensated by a quantity of transmitted light having the wavelength longer than the absorbable wavelength.

9 Claims, 2 Drawing Sheets

METHOD OF OPTICALLY MEASURING LIQUID IN POROUS MATERIAL

BACKGROUND OF THE INVENTION

1. Field of the Invention

The present invention relates to a method of optically measuring a liquid impregnated in a porous material, and in particular to a method of optically measuring a component of body liquid such as blood or urine.

2. Related Art

The so-called solid phase chemical analysis using test paper made of a porous material which has been previously impregnated with a reagent, has been used for measuring a component of body liquid such as blood or urine. The analysis for analyzing liquid impregnated in a solid material has been carried out by visually observing a degree of coloring of a porous material such as pH test paper, urine test paper, or blood sugar test paper which has been previously impregnated with a reagent, and which is impregnated with a liquid to be analyzed. Recently, measurement using a reflected light intensity method has been carried out in order to quantitatively detect a change in this coloring.

In general, an absorption spectrophotometry has been used for analyzing components in liquid, in which light is irradiated to the liquid, a quantity of light transmitted through the liquid is measured so as to obtain a ratio between a quantity of the irradiated light and a quantity of the transmitted light in order that the components are analyzed with the use of such a fact that the inverse logarithm of the quantity ratio between the irradiated light and the transmitted light is proportional to a concentration of the liquid. However, the absorption spectrophotometry is suitable for analyzing clear liquid, but is not suitable for analyzing muddy liquid or liquid impregnated in an opaque solid material. Accordingly, a specific wax method, a scattered light intensity method or an opal glass method has been used for analyzing muddy liquid, and a reflection spectrophotometry has been used for analyzing liquid impregnated in a solid material such as a porous material.

In the case of using the reflection spectrophotometry for analyzing liquid impregnated in a porous material or the like, random reflection at the outer surface of the porous material, a drawback such that a high degree of analyzing accuracy cannot be obtained due to unevenness in quantity of liquid in the vicinity of the outer surface of the porous material, or light absorption or the like of the porous material itself.

For example, U.S. Pat. No. 3,526,480 discloses an automatic analyzing device using the above-mentioned reflection spectrophotometry, but does not propose a countermeasure for resolving the above-mentioned problems.

Further, the U.S. Pat. No. 3,526,480 also discloses an automatic analyzing device in which light is transmitted through a porous material impregnated with liquid to be analyzed, in order to analyze the liquid with the use of transmitted light. In this apparatus, the porous material is impregnated with a reagent which is reacted with a sample, and the degree of coloring is obtained from an intensity ratio in transmitted light quantity with respect to the porous material as the object so as to carry out analysis for the liquid. However, even in this case, it is difficult to avoid affection caused by random reflection occurring at the outer surface of the porous material, unevenness in roughness of the porous material or the like.

SUMMARY OF THE INVENTION

The present invention is devised in order to solve the above-mentioned problems, and accordingly, an object of the present invention is to provide an optically measuring method in which a component in liquid impregnated in a porous material is measured with the use of transmitted light with no affection caused by the porous material.

To the end, according to the present invention, there is provided a method of measuring optical characteristics of liquid to be analyzed, which has been impregnated in a porous material, comprising the steps of preparing a light beam having an absorbable wavelength with which the light beam can be absorbed by an objective component in the liquid to be analyzed, and a light beam having a wavelength which is longer than the absorbable wavelength, projecting the light beam having the absorbable wavelength and the light beam having the longer wavelength onto the porous material impregnated with the liquid so as to allow the light beams to pass through the porous material, measuring quantities of the transmitted light beams having the absorbable wavelength and the longer wavelength, and compensating the quantity of the transmitted light having the absorbable wavelength with the use of the quantity of the transmitted light beam having the longer wavelength.

Nitrocellulose, acetylcellulose, filter paper, polyamide or the like in an organic material group, or glass fibers, silica gel or the like in an inorganic material group can be used as the porous material used in the present invention. In particular, nitrocellulose filter, acetylcellulose filter, glass fibers, filter paper, polyamide paper or the like is preferably used.

Further, in a method according to the present invention, a test specimen is reacted with a reagent impregnated in the porous material so that an objective component having produced optical absorption can be measured. As the reagent impregnated in the porous material, a biochemical item measuring reagent is used. For example, in such a case that the objective component is glucose, three kinds of materials that is, glucose oxidase, peroxidase and orthotrigin are used as the reagent. In such a case that the objective component is cholesterol, cholesterol oxidase, peroxidase, 4-aminoantipirin and phenol are used as the reagent.

Further, the present invention can be used for such measurement of optical absorption that one of a specific bonding couple is fixed while the other of the specific bonding couple is directly or indirectly bonded with a marker, and the other of the bonding couple is bonded to the fixed other of the bonding couple so that optical absorption exhibited by the trapped marker can be measured. As to the bonding couple, antigen-antibody, biotin-avidin, boronic acid-cis-diol group and the like may be used, and as the marker, a colored latex, gold colloid, selenium particles, fluorescein, rhodamine or the like which itself has a color may be used. Further, as a material which is colored by reaction, enzyme such as peroxidase, alkaline phosphatase, β-galactosidase, or the like can be used.

Preferably, the porous material is held between transparent plates during measurement so as to restrain surface reflection upon the porous material in order to enhance the accuracy of the measurement. As to the transparent plates, a plastic material made of polystyrene resin, polyether resin, polyethylene resin, polypropylene resin, polycarbonate resin, vinyl chloride resin, methacrylate resin or the like, or glass is used.

The present invention will be hereinbelow described in detail in the form of preferred embodiments with reference to the accompanying drawings in which:

DESCRIPTION OF PREFERRED EMBODIMENTS

Figure 1:
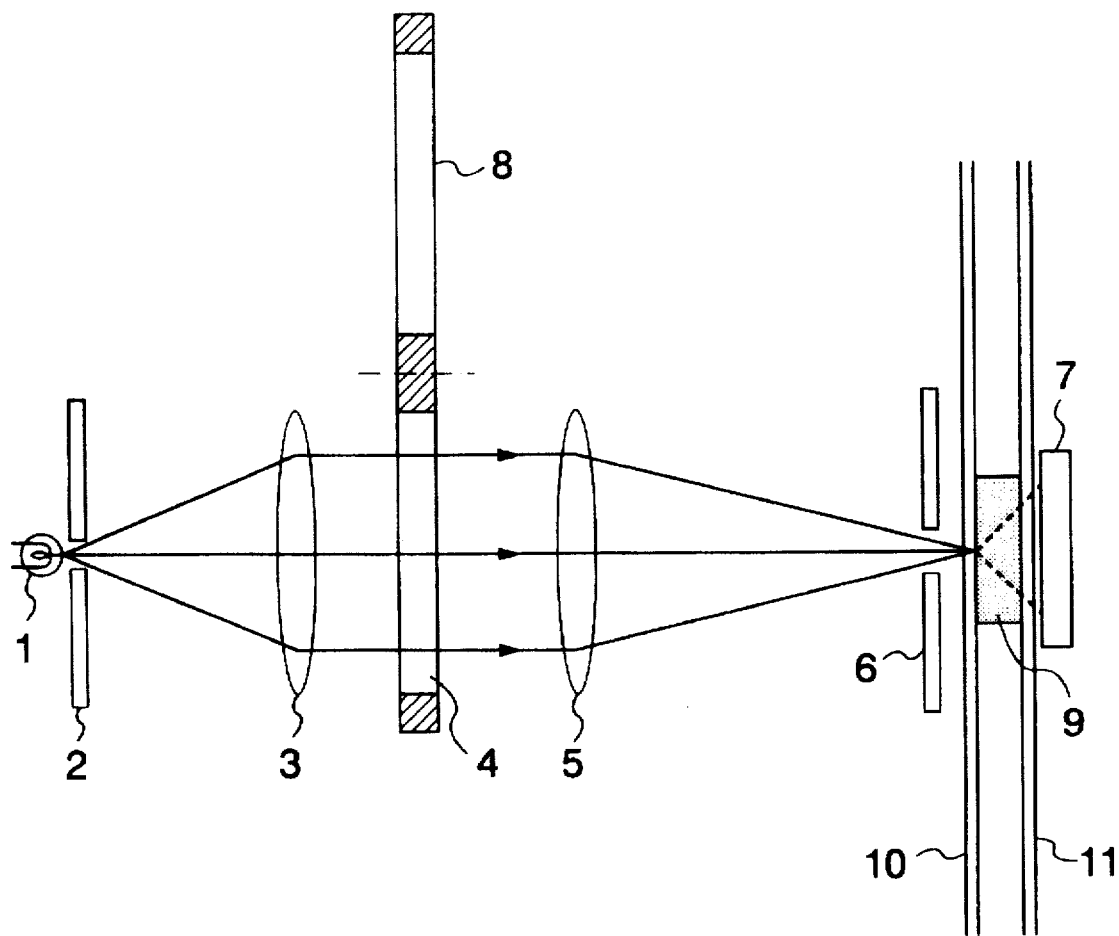
FIG. 1 is a schematic view illustrating an optical system used in a measuring method according to the present invention.

Referring to FIG. 1 which shows an example of a device used in a measuring method according to the present invention, the device composed of an optical system comprising a light source 1, a first slit 2, a first lens 3, filters 4, a second lens 5, a second slit 6 and a light receiver 7, and a filter rotor 8 for rotating the filters 4. The filter rotor 8 is provided therein with two kinds of filters one of which allows light having an absorbable wavelength for measuring an objective component to pass therethrough, and the other one of which allow light having a wavelength longer than the absorbable wavelength to pass therethrough.

A porous material 9 impregnated with liquid to be measured, is located at a focus of the second lens 5 between the second lens 5 and the light receiver 7. In this arrangement, it is preferable to hold the porous material 9 between transparent plates 10, 11 so as to restrain surface reflection at the porous material 9, and or to set the light receiver 7 near to the porous material 9 so as to receive scattered light from the porous material 9.

As to the light source 1, a tungsten lamp, a mercury lamp or the like is used, and as to the filters 4, interference filters are in general used. One of wavelengths which can transmits the filters, is preferably in a range of 700 to 800 nm in order to compensate the coarseness of the porous material, and the other wavelength is selected within a range of 400 to 700 nm in accordance with a reagent to be used. Instead of the interference filter, a color glass filter can be used. It is noted that a light beam is projected, perpendicular to the interference filter, when it is used, so as to maintain the accuracy of wavelength.

Further, in the case of using a light emitting diode as the light source, more than two kinds of light emitting diodes which emits light having desired wavelengths are used to irradiate the porous material so as to eliminate the necessity of a complicated optical system.

A slit is used for regulating the light beam. In the optical system shown in FIG. 1, the first slit 2 is arranged, adjacent to the light source 1, in order to prevent stray light entering the optical system. The second slit 6 regulates a light beam projected to the porous material.

Referring to FIG. 1, the light beam having passed through the first slit 2, is turned into parallel ray light by the first lens 3, and only light having specified wavelengths is transmitted through the filter 4. Thereafter, the light is converged by the second lens 5, and is then projected onto the porous material 9 after passing through the second slit 6. The transmitted light is detected by the light receiver 7.

Only light which is detected by the light receiver 7 is the one which is synchronized with the rotation of the filter, and the quantity of scattered light having been transmitted is compensated by a quantity of scattered light having been transmitted and having a wavelength longer than the measuring wavelength so as to obtain a measured value relating to the porous material 9.

The compensation for the porous material is made as follows. Liquid which does not contain a component to be measured is previously impregnated in the porous material so as to obtain the relationship between the light having a measuring wavelength and the light having a wavelength longer than the measuring wavelength is obtained so as to formulate a relationship expression. Then, a component to be measured is impregnated in the porous material so as to measure quantities of transmitted light with the measuring wavelength and the wavelength longer than the former, and the quantity of transmitted light having the measuring wavelength is compensated with the use of the relationship expression previously obtained.

Explanation will be hereinbelow made of reference examples of the present invention.

REFERENCE EXAMPLE 1

Measurement of Transmitted Light through Nitrocellulose Filter

Purified water was filled in a passage having a width of 4 mm and a thickness of 0.12 mm defined between two transparent plates one of which is formed therein with a groove, and the other one of which is planer, and a light beam having a wavelength of 630 nm was projected thereto so as to measure a quantity of transmitted light through the passage. The optical system shown in FIG. 1 is used for this measurement. A tungsten lamp is used as the light source while a phototransistor was used as the light receiver, and an output from the light receiver was amplified and was read by a voltmeter. Then, a nitrocellulose filter manufactured by Millipore Co., and having an averaged pore diameter of 8 μm was packed in a part of the passage, and purified water was filled in the passage. Then, quantities of transmitted light was measured with the use of two light beams having wavelengths of 630 nm and 750 nm.

Results of Measurements

A measured value (count value) of 8562.0 was obtained when the purified water was filled in the passage.

Measured values (count values) which were obtained by passing light beams having wavelengths of 630 nm and 750 nm through the passage in which the nitrocellulose filter was packed and filled with purified water are shown in Table 1.

TABLE 1

| Quantities of Transmitted Light through Nitrocellulose Filter | |
|---|---|
| 630 nm | 750 nm |
| 1 | 2298.124 | 2984.252 |
| 2 | 2457.824 | 3198.488 |
| 3 | 2287.668 | 2976.712 |
| 4 | 2384.948 | 3061.156 |
| 5 | 2265.880 | 2954.252 |
| 6 | 2249.760 | 2954.380 |
| 7 | 2314.888 | 3019.960 |
| 8 | 2247.048 | 2931.120 |
| 9 | 2195.480 | 2860.724 |

Figure 2:
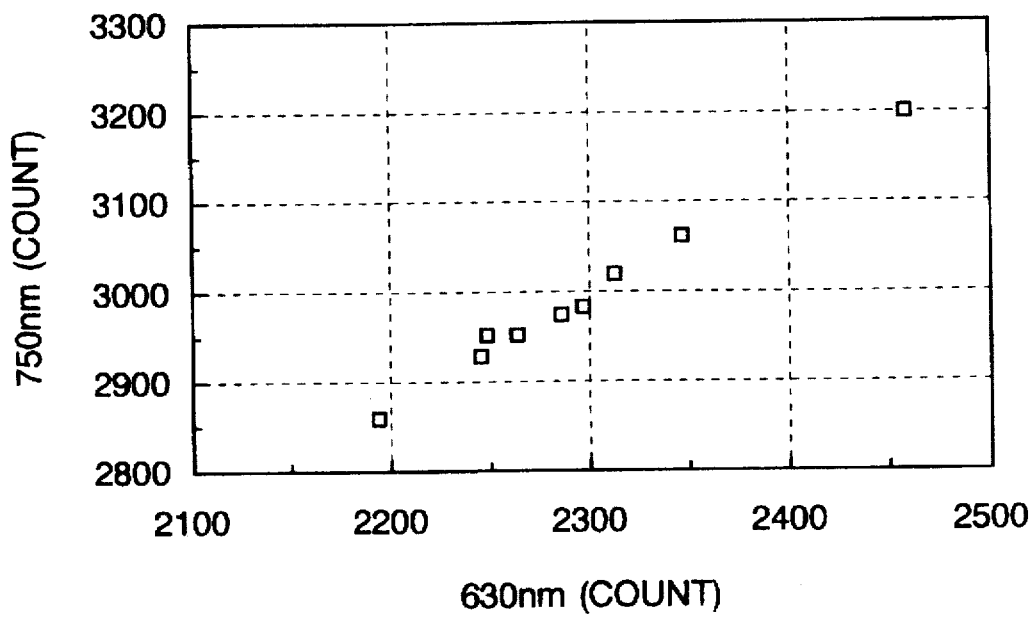
FIG. 2 is a view showing a correlation between wavelengths of transmitted light through purified water.

FIG. 2 is a graph in which measured values (count values) with the light beam having 630 nm are taken on X-axis, and measured values (counted values) with the light beam having 750 nm are taken on Y-axis. As understood from this graph, a substantially linear relationship is obtained therebetween. That is, this relationship in the graph can be exhibited by the following expression:

$Y=1.2624X+94.775(r=0.9959)$

This expression is used as a compensating expression.

REFERENCE EXAMPLE 2

Measured Value of Transmitted Light through Blue Aqueous Solution and Compensating Value therefor Similar to Reference Example 1, a nitrocellulose filter (Millipore Co.) having an averaged pore diameter of 8 μl was packed in a part of the passage, and an aqueous solution containing blue pigment was allowed to flow through the passage. The flow of the solution was stopped when the nitrocellulose filter was impregnated with the solution containing the blue pigment, and quantities of transmitted light from the nitrocellulose filter were measured with the use of light beams having 630 nm and 750 nm. Measurement was similar to that used in Reference Example 1. The aqueous solution containing the blue pigment impregnated in the nitrocellulose filter was obtained by solving a food blue color No. 1 in purified water so as to have pigment concentrations of 0.5, 1.0, 1.5, 2.0 and 3.0%. The measurement was repeated by ten times for each of the concentrations. The results of the measurements are shown in Table 2:

TABLE 2

Quantities of Transmitted Light through Aqueous Solution containing Blue Pigment

|  | 0.5% Pigment | | 1.0% Pigment | | 1.5% Pigment | |
| --- | --- | --- | --- | --- | --- | --- |
|  | 630 nm | 630/750 | 630 nm | 630/750 | 630 nm | 630/750 |
| Averaged Value | 0.3792 | 0.3724 | 0.6605 | 0.6505 | 0.8838 | 0.8852 |
| Standard Deviation | 0.0185 | 0.0052 | 0.0109 | 0.0077 | 0.0146 | 0.0057 |
| Variation Variable | 4.8809 | 1.4066 | 1.6629 | 1.1853 | 1.6527 | 0.6544 |

|  | 2.0% Pigment | | 3.0% Pigment | |
| --- | --- | --- | --- | --- |
|  | 630 nm | 630/750 | 630 nm | 630/750 |
| Averaged Value | 1.1039 | 1.0881 | 1.469 | 1.447 |
| Standard Deviation | 0.0088 | 0.0063 | 0.0095 | 0.0090 |
| Variation Variable | 0.8056 | 0.5789 | 0.6479 | 0.6235 |

The values in the column of 630 nm in Table 2 were obtained by dividing measured values (count values) of transmitted light through the pigments having respective concentrations with the use of a light beam having 630 nm, into 2296.2 which was obtained by transmitting the light beam having 630 nm through the purified water (that is, an averaged value of measured values obtained in Reference Example 1 with the light beam having 630 nm transmitted through the nitrocellulose filter impregnated with purified water), and then by logarithmically converting the thus divided values. Further, the values in the column of 630/750 in Table 2 were obtained by dividing the measured values (count values) of the solution containing the blue pigment at 630 nm into count values of purified water at 630 nm, which were obtained from measured values (count values) of the pigment concentrations at 750 nm, by using the relationship expression obtained in Reference Example 1, and by compensating and logarithmically converting thus obtained values. That is, the measured values (count values) at 630 nm were compensated with the measured values (count values) at 750 nm, and were logarithmically converted.

From the standard deviations and the variation variables in Table 2, it is understood that the reproducibility can be enhanced by the compensation with the use of the measured values at 750 nm. This shows an effect such that unevenness among measured values due to variation in coarseness of the porous material can compensated.

Figure 3:
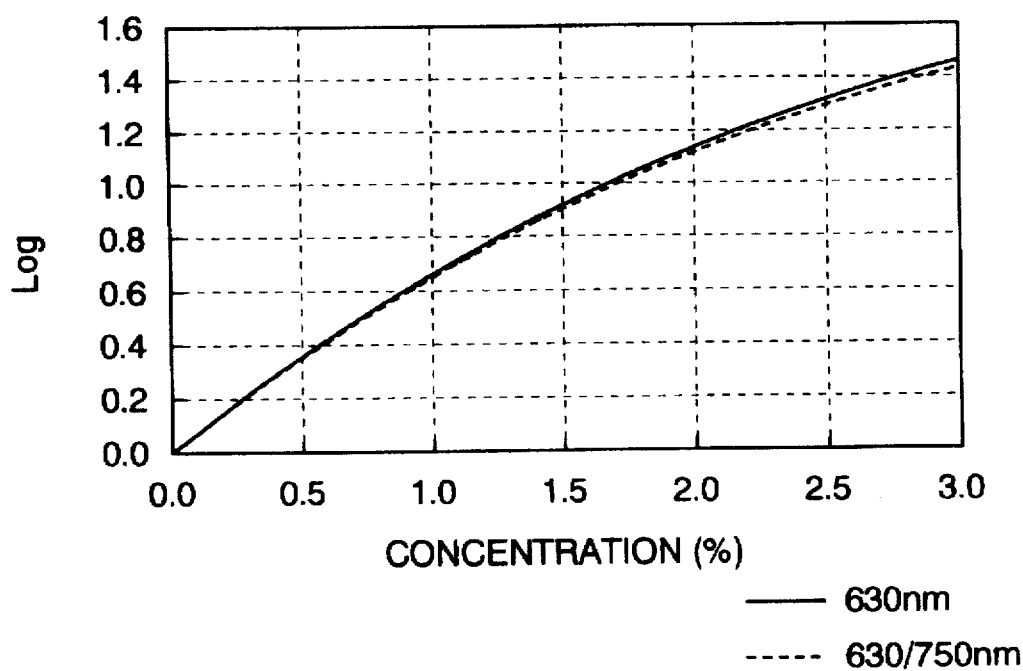
FIG. 3 is a view showing relationship between concentrations and measured values.

FIG. 3 is a graph in which data listed in Table 2 are plotted.

A curve in FIG. 3 can maintain its gradient even around 3% concentration. Meanwhile, the quantity of transmitted light through 3% blue pigment solution was converted into a count value of $2296.2 \times 10^{-1.469}$, which corresponds to a quantity of transmitted light of about 1% at a count value of 8562.0 in the case of the purified water. That is, in the method according to the present invention, even about 1% of transmitted light quantity can be measured in consideration with the gradient of the curve shown in FIG. 3.

As mentioned above, in the method according to the present invention, the light beams having a wavelength which is absorbed by a liquid impregnated in the porous material and a wavelength which is not absorbed thereby are projected, and quantities of transmitted light obtained respectively from these light beams are measured, and the measured values obtained by the absorbed wavelength are compensated by the measured value obtained by the unabsorbed wavelength. Thus, it is possible to reduce the affection caused by variation in coarseness of the porous material which is inherent to the prior art, thereby the problem of low reproducibility of measured value can be solved.

What is claimed is:

1. A method of measuring optical characteristics of a liquid to be measured impregnated in a porous material, comprising the steps of preparing a light beam having an absorbable wavelength with which the light beam is absorbed by an objective component in the liquid to be measured, and a light beam having a wavelength longer than the absorbable wavelength; projecting both light beams onto the porous material impregnated with the liquid to be measured so as to pass said both light beams through the porous material; measuring quantities of transmitted light having the absorbable wavelength and the wavelength longer than the former, and compensating the quantity of transmitted light having the absorbable wavelength with the quantity of transmitted light having the longer wavelength.

2. A method as set forth in claim 1, wherein the light beam having the absorbable wavelength and the light beam having the longer wavelength are projected to a liquid which does not contain the objective component so as to obtain a relationship between quantities of transmitted light having the absorbable wavelength and the longer wavelength, and the quantity of transmitted light having the wavelength which is absorbed by the objective component is compensated with said relationship.

3. A method as set forth in claim 1 or 2, wherein said porous material is the one which is selected from the group consisting of nitrocellulose, acetylcellulose, glass fibers, filter paper and polyamide.

4. A method as set forth in claim 1 or 2, wherein a test specimen is reacted with a reagent carried by said porous material so as to measure the objective component whose optical absorptive characteristics are visible thereby.

5. A method as set forth in claim 1 or 2, wherein one of a couple of specified bonds is fixed, and the other one of the couple of specified bonds is directly or indirectly coupled with a marker, and the other one of the couple is coupled with the fixed one of the couple, and an optical absorption exhibited by the trapped marker is measured.

6. A method as set forth in claim 1 or 2, wherein said porous material is held between transparent plates.

7. A method as set forth in claim 3, wherein said porous material is held between transparent plates.

8. A method as set forth in claim 4, wherein said porous material is held between transparent plates.

9. A method as set forth in claim 5, wherein said porous material is held between transparent plates.

* * * * *